(12) United States Patent
Deluca et al.

(10) Patent No.: US 11,260,241 B2
(45) Date of Patent: Mar. 1, 2022

(54) METHOD OF TREATING MULTIPLE SCLEROSIS

(71) Applicant: Wisconsin Alumni Research Foundation, Madison, WI (US)

(72) Inventors: Hector F. Deluca, Deerfield, WI (US); Bryan R. Becklund, San Diego, CA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 265 days.

(21) Appl. No.: 16/131,544

(22) Filed: Sep. 14, 2018

(65) Prior Publication Data

US 2019/0009104 A1  Jan. 10, 2019
US 2019/0381335 A9  Dec. 19, 2019

Related U.S. Application Data

(63) Continuation-in-part of application No. 13/773,254, filed on Feb. 21, 2013, now Pat. No. 10,780,295, and a continuation of application No. 13/576,253, filed as application No. PCT/US2011/023608 on Feb. 3, 2011, now abandoned.

(60) Provisional application No. 61/663,401, filed on Jun. 22, 2012, provisional application No. 61/301,820, filed on Feb. 5, 2010.

(51) Int. Cl.
 *A61N 5/06*  (2006.01)

(52) U.S. Cl.
 CPC ......... *A61N 5/0618* (2013.01); *A61N 5/0613* (2013.01); *A61N 2005/0661* (2013.01)

(58) Field of Classification Search
 CPC ................ A61N 5/0618; A61N 5/0613; A61N 2005/0661; A61N 2005/064; A61N 5/0616
 See application file for complete search history.

(56) References Cited

U.S. PATENT DOCUMENTS

| 7,985,219 B2 | 7/2011 | Wilkens et al. |
| 8,287,524 B2 | 10/2012 | Sigel |
| 2003/0045916 A1 | 5/2003 | Anderson et al. |
| 2005/0085878 A1 | 4/2005 | Wilkens et al. |
| 2006/0013454 A1 | 1/2006 | Flewelling et al. |

(Continued)

FOREIGN PATENT DOCUMENTS

| CA | 2435916 | 9/2002 |
| WO | 2008061197 A2 | 5/2008 |

(Continued)

OTHER PUBLICATIONS

Chel, et al., Ultraviolet Irradiation Corrects Vitamin D Deficiency and Suppresses Secondary Hyperparathyroidism in the Elderly, Journal of Bone and Mineral Research, 1998, 13(8):1238-1242.

(Continued)

*Primary Examiner* — Shirley X Jian
(74) *Attorney, Agent, or Firm* — Quarles & Brady LLP (57) ABSTRACT

A method and computer program product for suppressing the symptoms of multiple sclerosis (MS) by irradiating a subject exhibiting the symptoms with a pre-determined dose of UV-containing light from a light source and detecting a suppression of the clinical symptoms of MS. In particular, the detected suppression of the clinical symptoms is disassociated from the vitamin D production within the subject.

10 Claims, 3 Drawing Sheets

(56) References Cited

U.S. PATENT DOCUMENTS

| | | | |
|---|---|---|---|
| 2006/0292182 A1 | 12/2006 | Kemeny et al. | |
| 2007/0106284 A1 | 5/2007 | Siegel | |
| 2007/0179570 A1* | 8/2007 | De Taboada | A61H 23/0245 607/88 |
| 2007/0179571 A1* | 8/2007 | De Taboada | A61N 5/0622 607/88 |
| 2007/0185553 A1 | 8/2007 | Kennedy | |
| 2008/0014176 A1 | 1/2008 | Di Mauro et al. | |
| 2008/0221211 A1* | 9/2008 | Streeter | A61N 5/0613 514/557 |
| 2008/0224592 A1 | 9/2008 | Reich et al. | |
| 2009/0221538 A1 | 9/2009 | Hayes et al. | |
| 2010/0121420 A1 | 5/2010 | Fiset et al. | |
| 2011/0238140 A1 | 9/2011 | Kurkayev | |
| 2012/0071954 A1* | 3/2012 | Kao | A61N 5/0613 607/88 |

FOREIGN PATENT DOCUMENTS

| | | |
|---|---|---|
| WO | 2008136958 A1 | 11/2008 |
| WO | 2011097383 A1 | 8/2011 |
| WO | 2013072701 A | 5/2013 |

OTHER PUBLICATIONS

Tejasvi, et al., Determination of Minimal Erythemal Dose for Narrow Band-Ultraviolet B Radiation in North Indian Patients: Comparison of Visual and Dermaspectrometer Readings, Indian Journal of Dermatology, Venereology and Leprology, 2007, 73(2):97-99.

International Search Report and Written Opinion dated Mar. 23, 2011 in connection with PCT/US2011/023608.

European Patent Office, International Search Report issued in PCT/US2013/044435; dated Aug. 23, 2013.

Agranoff, et al., Diet and the Geographical Distribution of Multiple Sclerosis, Lancet, 1974, 2(7888):1061-1066.

Becklund, et al., UV Radiation Suppresses Experimental Autoimmune Encephalomyelitis Independent of Vitamin D Production, Proc Natl Acad Sci USA, 2010, 107(14):6418-6423.

Cantorna, et al., 1,25-Dihydroxyvitamin D3 Reversibly Blocks the Progression of Relapsing Encephalomyelitis, A Model of Multiple Sclerosis, Proc Natl Acad Sci USA, 1996, 93(15):7861-7864.

Cantorna, et al., Dietary Calcium is a Major Factor in 1,25-dihydroxycholecalciferol Suppression of Experimental Autoimmune Encephalomyelitis in Mice, J Nutr, 1999, 129(11):1966-1971.

Cavaletti, et al., Extracorporeal Photochemotherapy Reduces the Severity of Lewis Rat Experimental Allergic Encephalomyelitis through a Modulation of the Function of Peripheral Blood Mononuclear Cells, J Biol Regul Homeost Agents, 2004, 18(1):9-17.

Correale, et al., Immunomodulatory Effects of Vitamin D in Multiple Sclerosis, Brain, 2009, 132:1146-1160.

Hauser, et al., Prevention of Experimental Allergic Encephalomyelitis (EAE) in the SJL/J Mouse by Whole Body Ultraviolet Irradiation, J Immunol, 1984, 132(3):1276-1281.

Lemire, et al., 1,25-dihydroxyvitamin D3 Prevents the In Vivo Induction of Murine Experimental Autoimmune Encephalomyelitis, J Clin Invest, 1991, 87(3):1103-1107.

Meehan, et al., Hypercalcemia Produced by Parathyroid Hormone Suppresses Experimental Autoimmune Encephalomyelitis in Female but not Male Mice, Arch Biochem Biophys, 2005, 442(2):214-221.

Runia, et al., Lower Serum Vitamin D Levels are Associated with a Higher Relapse Risk in Multiple Sclerosis, Neurology, 2012, 79(3):261-266.

Wang, et al., Development of Experimental Autoimmune Encephalomyelitis (EAE) in Mice Requires Vitamin D and the Vitamin D Receptor, Proc Natl Acad Sci USA, 2012, 109(22):8501-8504.

Wang, et al., Suppression of Experimental Autoimmune Encephalomyelitis by 300-315 nm Ultraviolet Light, Archives of Biochemistry and Biophysics, 2013, 536:81-86.

European Patent Office, Extended European Search Report, Application No. 11740357.6, dated Sep. 16, 2013, 6 pages.

European Patent Office, Communication, Application No. 11740357.6, dated May 20, 2014, 4 pages.

European Patent Office, Communication, Application No. 11740357.6, dated Dec. 9, 2014, 3 pages.

European Patent Office, Communication, Application No. 13733128.6, dated Mar. 20, 2017, 4 pages.

European Patent Office, Communication, Application No. 13733128.6, dated Oct. 17, 2017, 3 pages.

European Patent Office, Extended European Search Report, Application No. 17204747.4, dated Apr. 16, 2018, 6 pages.

Tsunoda et al., "Converting relapsing remitting to secondary progressive experimental allergic encephalomyelitis (EAE) by ultraviolet B irradiation", Nov. 2004, Journal of Neuroimmunology, vol. 160, pp. 122-134.

* cited by examiner

METHOD OF TREATING MULTIPLE SCLEROSIS

CROSS-REFERENCE TO RELATED APPLICATIONS

This patent application is a Continuation-in-Part Application of U.S. Ser. No. 13/773,254, filed Feb. 21, 2013, which application claims the benefit of U.S. Provisional Patent Application No. 61/663,401, filed Jun. 22, 2012, and is a Continuation Application of Ser. No. 13/576,253 filed Jul. 31, 2012, which is the national stage application of PCT/US2011/023608, filed Feb. 3, 2011 (now published as WO 2011/097383), which claims the benefit of U.S. Provisional Patent Application No. 61/301,820, filed Feb. 5, 2010. Each application is incorporated by reference herein in its entirety for all purposes and, in particular, to provide description of system and method for irradiation of a subject with UV light.

BACKGROUND OF THE INVENTION

Multiple sclerosis (MS) is a chronic and often debilitating disease affecting approximately 2.5 million people worldwide (Compston A & Coles A, 2002, Multiple sclerosis, *Lancet* 359(9313):1221-1231). The hallmark pathological characteristic of MS is the formation of inflammatory plaques in the central nervous system. The plaques contain a number of immune cells which are believed to orchestrate the autoimmune-mediated destruction of the myelin sheath surrounding neuronal axons (Noseworthy J H, Lucchinetti C, Rodriguez M, and Weinshenker B G, 2000, Multiple sclerosis. *N Engl J Med* 343(13):938-952). Demyelination leads to altered neuronal signal conduction and a myriad of adverse neurological symptoms.

Although the exact cause of MS is unknown, a number of genetic and environmental factors are thought to influence MS development (Ebers G C, 2008, Environmental factors and multiple sclerosis. *Lancet Neurol* 7(3):268-277). Epidemiological studies have demonstrated that MS incidence typically follows a latitudinal gradient in both hemispheres. In the northern hemisphere, including Europe and North America, MS is more common in the northern regions, whereas in the southern hemisphere, including Australia MS is more prevalent in the southern regions (Ebers G C and Sadovnick A D, 1993, The geographic distribution of multiple sclerosis: a review. *Neuroepidemiology* 12(1):1-5). This apparent correlation or "latitude gradient" has led to speculation that because sunlight exposure decreases with increased latitude, decreased sunlight exposure may be an underlying cause of the MS latitude gradient (Acheson E D, Bachrach C A, and Wright F M, 1960, Some comments on the relationship of the distribution of multiple sclerosis to latitude, solar radiation, and other variables. *Acta Psychiatr Scand Suppl* 35(147):132-147). Findings that the average annual hours of sunlight exposure in an individual's place of birth is inversely correlated with MS development support this hypothesis (Acheson E D, Bachrach C A, and Wright F M, 1960, Some comments on the relationship of the distribution of multiple sclerosis to latitude, solar radiation, and other variables. *Acta Psychiatr Scand Suppl* 35(147):132-147; and Sutherland J M, Tyrer J H, and Eadie M J, 1962, The prevalence of multiple sclerosis in Australia. *Brain* 85:149-164). Furthermore, individuals with the highest residential and occupational solar exposure have the lowest rate of MS incidence (Freedman D M, Dosemeci M, and Alavanja M C, 2000, Mortality from multiple sclerosis and exposure to residential and occupational solar radiation: a case-control study based on death certificates. *Occup Environ Med* 57(6):418-421). These results suggest that decreased sunlight exposure may be a significant environmental factor contributing to the development of MS.

The sun emits a wide range of electromagnetic radiation, including ultraviolet (UVR) (100-400 nm), visible (400-800 nm), and infrared (≥800 nm) radiation. Exposure to all radiation has profound impacts on human health. For instance, UVR can cause direct damage to DNA and is a leading cause of skin carcinomas. In addition to directly damaging DNA, UVR can induce carcinogenesis by suppressing the immune system (Fisher M S and Kripke M L, 1977, Systemic alteration induced in mice by ultraviolet light irradiation and its relationship to ultraviolet carcinogenesis. *Proc Natl Acad Sci U S A* 74(4):1688-1692; and Kripke M L, 1974, Antigenicity of murine skin tumors induced by ultraviolet light. *J Natl Cancer Inst* 53(5):1333-1336).

UVR can also be absorbed by photoreceptors in human cells, resulting in the release of a number of secondary mediators capable of suppressing cell-mediated immunity through multiple mechanisms (Leitenberger J, Jacobe H T, and Cruz P D, Jr., 2007, Photoimmunology—illuminating the immune system through photobiology. *Semin Immunopathol* 29(1):65-70). These mechanisms lead to both local and systemic immunosuppression, thereby eliminating natural defense mechanisms against aberrant cell growth.

Although UV-induced immunosuppression clearly has detrimental effects in the context of skin cancer, it may have beneficial effects on organ-specific autoimmune diseases such as MS (McMichael A J and Hall A J, 1997, Does immunosuppressive ultraviolet radiation explain the latitude gradient for multiple sclerosis? *Epidemiology* 8(6):642-645). A recent study demonstrated that MS relapse rates are lower in the summer than in the winter, suggesting UV exposure may be a contributing factor in relapses (Tremlett H et al., 2008, Monthly ambient sunlight, infections and relapse rates in multiple sclerosis. *Neuroepidemiology* 31(4):271-279). Furthermore, experiments conducted in the experimental autoimmune encephalomyelitis (EAE) animal model of MS have demonstrated that seven-day pretreatment with UVR prevents disease induction in SJL mice (Hauser S L et al., 1984, Prevention of experimental allergic encephalomyelitis (EAE) in the SJL/J mouse by whole body ultraviolet irradiation. *J Immunol* 132(3):1276-1281). Our attempt to reproduce the preventative effect of irradiation discussed in the above-mentioned study demonstrated no protective effect (see FIG. 1 and the related description below). Thus, while avoiding UVR exposure may reduce the risk of various skin cancers, it could inadvertently increase the risk of developing autoimmune diseases such as MS.

UVR also modulates the immune response by stimulating the endogenous production of vitamin D in the skin. UVB wavelengths between 270 and 300 nm stimulate the production of pre-vitamin $D_3$ from the cholesterol derivative 7-dehydrocholesterol (Jones G, Strugnell S A, and DeLuca H F, 1998, Current understanding of the molecular actions of vitamin D. *Physiological Reviews* 78(4):1193-1231). Pre-vitamin $D_3$ undergoes a spontaneous isomerization to produce vitamin $D_3$. Vitamin $D_3$ undergoes two successive hydroxylation steps to form the active hormone 1α,25-dihydroxyvitamin $D_3$ ($1,25(OH)_2D_3$). The first activation step occurs in the liver, where vitamin $D_3$ is hydroxylated at carbon-25 to generate 25-hydroxyvitamin $D_3$ ($25(OH)D_3$) (Blunt J W, DeLuca H F, and Schnoes H K, 1968, 25-hydroxycholecalciferol. A biologically active metabolite of vitamin $D_3$. *Biochemistry* 7(10):3317-3322). The 25(OH)$D_3$ metabolite is the primary circulating form of vitamin $D_3$ and is commonly used as a clinical indicator of vitamin D status (DeLuca H F, 2004, Overview of general physiologic features and functions of vitamin D. *Am J Clin Nutr* 80(6 Suppl):1689S-1696S). The second activation step occurs in the kidney and involves the stereospecific hydroxylation of 25(OH)$D_3$ at carbon-1 to yield 1,25(OH)$_2D_3$ (Holick M F, Schnoes H K, and DeLuca H F, 1971, Identification of 1,25-dihydroxycholecalciferol, a form of vitamin $D_3$ metabolically active in the intestine. *Proc Natl Acad Sci USA* 68(4):803-804; and Fraser D R and Kodicek E, 1970, Unique biosynthesis by kidney of a biological active vitamin D metabolite. *Nature* 228(5273):764-766). The classical biological function of 1,25(OH)$_2D_3$ is to maintain sufficient serum calcium and phosphorus levels for proper mineralization of bone and calcium for neuromuscular function.

In addition to its role in regulating serum calcium levels, vitamin D may also be an environmental factor in MS and other autoimmune diseases (Hayes C E, Nashold F E, Spach K M, and Pedersen L B, 2003, The immunological functions of the vitamin D endocrine system. *Cell Mol Biol (Noisy-le-grand)* 49(2):277-300). The potential link between vitamin D deficit and MS was first proposed by David Goldberg, based on the geographic "latitude gradient" distribution patterns of MS and the relationship between UVR and vitamin D production (Goldberg P, 1974, Multiple Sclerosis: Vitamin D and calcium as environmental determinants of prevalence (a viewpoint). Part 1: Sunlight, dietary factors, and epidemiology. *International Journal of Environmental Studies* 6:19-27). Goldberg postulated that decreased exposure to UVR and subsequent vitamin D insufficiency at higher latitudes pre-disposes individuals residing in these regions to developing MS.

Much of the evidence supporting this hypothesis is derived from epidemiological data demonstrating an association between UVR and MS prevalence and the assumption that the immunosuppressive effects of UVR are mediated through vitamin D production. However, UVR suppresses the immune system through mechanisms independent of vitamin D (Lucas R M and Ponsonby A L, 2006, Considering the potential benefits as well as adverse effects of sun exposure: can all the potential benefits be provided by oral vitamin D supplementation? *Prog Biophys Mol Biol* 92(1):140-149). Therefore, this assumption may not be valid.

Additional evidence suggesting that vitamin D may play a role in MS stems from population-based studies which have correlated high serum 25(OH)$D_3$ levels with a decreased risk for developing MS (Munger K L, Levin L I, Hollis B W, Howard N S, and Ascherio A, 2006, Serum 25-hydroxyvitamin D levels and risk of multiple sclerosis. *Jama* 296(23):2832-2838). However, since 25(OH)$D_3$ levels largely reflect an individual's exposure to UVR, it is impossible to determine if the decreased risk is attributable specifically to vitamin D or UVR.

Perhaps the most compelling evidence supporting a role for vitamin D in MS is derived from studies conducted using the experimental autoimmune encephalomyelitis (EAE) model of MS. A number of in vivo studies have demonstrated that 1,25(OH)$_2D_3$ can suppress disease induction and progression in the EAE model of MS (Lemire J M and Archer D C, 1991, 1,25-dihydroxyvitamin $D_3$ prevents the in vivo induction of murine experimental autoimmune encephalomyelitis. *J Clin Invest* 87(3):1103-1107; Cantorna M T, Hayes C E, and DeLuca H F, 1996, 1,25-Dihydroxyvitamin $D_3$ reversibly blocks the progression of relapsing encephalomyelitis, a model of multiple sclerosis. *Proc Natl Acad Sci USA* 93(15):7861-7864; and Nashold F E, Hoag K A, Goverman J, and Hayes C E, 2001, Rag-1-dependent cells are necessary for 1,25-dihydroxyvitamin D(3) prevention of experimental autoimmune encephalomyelitis. *J Neuroimmunol* 119(1):16-29). However, complete disease suppression is only achieved using supraphysiological doses of 1,25(OH)$_2D_3$ which cause vitamin D toxicity and hypercalcemia (Cantorna M T, Humpal-Winter J, and DeLuca H F, 1999, Dietary calcium is a major factor in 1,25-dihydroxycholecalciferol suppression of experimental autoimmune encephalomyelitis in mice. *Journal of Nutrition* 129(11): 1966-1971). Vitamin D toxicity and hypercalcemia do not typically occur upon exposure to sunlight due to a number of factors that limit the endogenous production of vitamin D. These factors include the photochemical conversion of previtamin $D_3$ into biologically inert compounds, skin pigmentation, and latitude (Holick M F, MacLaughlin J A, and Doppelt S H, 1981, Regulation of cutaneous previtamin $D_3$ photosynthesis in man: skin pigment is not an essential regulator. *Science* 211(4482):590-593). Thus, the levels of 1,25(OH)$_2D_3$ required to suppress MS are well above those that can be produced naturally upon exposure to sunlight. Furthermore, results from our laboratory suggest that hypercalcemia may be more than simply an unfortunate consequence of 1,25(OH)$_2D_3$ treatment, and may play an essential role in the immunosuppressive effects of 1,25(OH)$_2D_3$ (Meehan T F, Vanhooke J, Prahl J, and Deluca H F, 2005, Hypercalcemia produced by parathyroid hormone suppresses experimental autoimmune encephalomyelitis in female but not male mice. *Arch Biochem Biophys* 442(2): 214-221).

Considering the undesired effects that large doses of vitamin D, which are associated with reduction of clinical parameters of MS, there exists a need for a methodology for suppressing symptoms of MS without the dangerous and unpleasant side effects associated with 1,25(OH)$_2D_3$ treatment.

SUMMARY OF THE INVENTION

Embodiments of the invention address methods and apparatus for treating and preventing MS that encompass irradiating the subject with a first dose of light from a light source and detecting a suppression of the clinical symptoms in the subject. According to the embodiments, irradiation is generally characterized by a chosen dose of radiation and repetition time intervals, and, in a specific embodiment, may be continuous. In one embodiment, irradiating a subject with light, preferably UV light, is adapted to be unassociated with permanently elevated levels of vitamin D and independent from production of vitamin D in the irradiated subject.

In one embodiment, the present invention comprises a method of suppressing clinical symptoms of multiple sclerosis comprising irradiating the subject with a first dose of light from a light source and detecting a suppression of the clinical symptoms in this subject. The irradiation may either be with repeated doses or a continuous dose.

One embodiment of the present invention provides a method for suppressing clinical symptoms of MS in a subject having a reference level of serum calcium and a reference level of a serum 25(OH)$D_3$. Such method includes irradiating the subject with such a first dose of light from a light source that is adapted to cause a change of a serum 25(OH)$D_3$ level in the subject from the reference level of a serum 25(OH)$D_3$ to a first level that is lower than a threshold level associated with suppression of the clinical symptoms.

In addition, such method may include repeatedly irradiating the subject at repetition time intervals with a second dose of light from the light source. Here, the second dose and repetition time intervals are judiciously chosen as to maintain a serum $25(OH)D_3$ level below the threshold level. Repeatedly irradiating the subject may require, in one implementation, irradiating with the second dose for at least 10 minutes every 24 hours for seven days. Furthermore, the embodiment includes detecting a suppression of the clinical symptoms that is independent of a vitamin D production in the subject. These repeated doses may be, part of a continuous dose.

In one specific embodiment, the first dose may be further adapted to maintain the level of serum calcium within 0.5 mg/dL with respect to the reference level of serum calcium, while the second dose and repetition time intervals may be further adapted to cause variation of a serum $25(OH)D_3$ level by no more than 5 ng/mL. In another specific embodiment, each of the first and second doses of light is associated with UV irradiance of at least 2.5 $kJ/m^2$ and, alternatively or in addition, with UVB irradiance of at least 2.5 $kJ/m^2$.

The suppression of clinical symptoms of MS, according to one embodiment, includes at least one of a decrease of the cumulative disease index (CDI), a delay of onset of MS symptoms, and a reduction of peak of severity of MS symptoms, and, in particular, delay or reduction in the appearance of plaques or lesions.

Without the loss of generality, each of the embodiments of the method of the invention may further include identifying the subject with the use of pre-defined diagnostic criteria.

Embodiments of the invention further provide a computer program product for use on a computer system for irradiating a subject, having a reference level of serum calcium and a reference level of a serum $25(OH)D_3$, with light from a light source and detecting changes in at least one of a level of serum calcium and a level of a serum $25(OH)D_3$, where the computer program product includes a computer usable tangible medium having computer readable program code thereon, and where the computer readable program code includes at least a) program code for irradiating the subject with a first dose of light from a light source, the first dose being adapted to cause a change of a serum $25(OH)D_3$ level from the reference level of a serum $25(OH)D_3$ to a first level that is lower than a threshold level associated with suppression of the clinical parameters; and b) program code for repeatedly irradiating the subject, oriented with respect to a light source, at repetition time intervals with a second dose of light from the light source, the second dose and repetition time intervals being such as to maintain a serum $25(OH)D_3$ level below the threshold level.

In one embodiment, the program code for irradiating the subject with a first dose includes program code for administering the first dose adapted to maintain the level of serum calcium within 0.5 mg/dL with respect to the reference level of serum calcium. In addition or alternatively, the program code for repeatedly irradiating the subject includes program code for defining such second dose and repetition time intervals as to not cause variation of a serum $25(OH)D_3$ level in excess of 5 ng/mL.

Embodiments of the invention additionally provide a computer program product for use on a computer system for irradiating a subject having MS with light from a light source, where the computer program product includes a computer usable tangible medium having computer readable program code thereon, which, when loaded into the computer system, establishes an apparatus, implemented in the computer system, the apparatus comprising at least an input for receiving a set of energy data characterizing exposure to light prescribed to the subject and a processor that operates to determine at least one of components of the light source and location of said components based on the received set of energy data. In addition, in one embodiment, the apparatus may include an output, in which appears a display of results of the prescribed exposure of the subject to light.

BRIEF DESCRIPTION OF THE DRAWINGS

The invention will be more fully understood by referring to the following Detailed Description of Specific Embodiments in conjunction with the Drawings, of which.

DETAILED DESCRIPTION OF THE INVENTION

When used in the specification and in the appended claims, certain terms will have meanings according to the definitions provided below, unless context requires otherwise:

The terms "including" and "comprising" are open-ended terms and should be interpreted to mean "including, but not limited to . . . ." These terms encompass the more restrictive terms "consisting essentially of" and "consisting of."

The singular forms "a", "an", and "the" include plural reference. As well, the terms "a" (or "an"), "one or more"

and "at least one" can be used interchangeably. The terms "comprising", "including", "characterized by" and "having" can be used interchangeably.

Unless defined otherwise, all technical and scientific terms used herein have the same meanings as commonly understood by one of ordinary skill in the art to which this invention belongs. Each of the publications and patent documents specifically mentioned herein is incorporated by reference in its entirety for all purposes including describing and disclosing the chemicals, instruments, statistical analyses and methodologies which are reported in the publications and which might be used in connection with the invention. All references cited in this specification are to be taken as indicative of the level of skill in the art. Nothing herein is to be construed as an admission that the invention is not entitled to antedate such disclosure by virtue of prior invention.

Although the exact cause of multiple sclerosis (MS) is unknown, a number of genetic and environmental factors are thought to influence MS susceptibility. One potential environmental factor is sunlight and the subsequent production of vitamin D. A number of studies have correlated decreased exposure to ultraviolet radiation (UVR) and low serum 25-hydroxyvitamin $D_3$ (25(OH)$D_3$) levels with an increased risk for developing MS. However, it is unclear whether UVR, vitamin D, or both are necessary for the putative decrease in MS susceptibility. The embodiments of the invention, as shown in the Examples below, illustrated the ability of UVR to suppress disease in the EAE model of MS and allowed to assess the effect of UVR on serum 25(OH)$D_3$ and calcium levels. Our results indicated that repeated treatment with UVR, such as daily treatment, for example, dramatically suppresses clinical signs of EAE. More importantly, such suppression was associated with only a modest, transient increase in serum 25(OH)$D_3$ levels which were insufficient to suppress EAE independent of UVR treatment. These results suggest that UVR is likely suppressing disease independent of vitamin D production and that vitamin D supplementation alone may not replace the ability of sunlight to reduce MS susceptibility. Identification of a subject or patient appropriate for treatment of MS symptoms can be carried out based on standardized diagnostic criteria widely used by practicing physicians, specially in the first stages of the disease, such as the so-called Schumacher and Poser criteria (Compston A, Coles A, October 2008, "Multiple sclerosis". *Lancet* 372 (9648): 1502-17; Trojano M, Paolicelli D, November 2001. "The differential diagnosis of multiple sclerosis: classification and clinical features of relapsing and progressive neurological syndromes". *Neurol. Sci.* 22 (Suppl 2): S98-102; and Poser C M, Brinar V V, June 2004, "Diagnostic criteria for multiple sclerosis: an historical review". *Clin Neurol Neurosurg* 106 (3): 147-58), or the McDonald criteria, which focus on a demonstration with clinical, laboratory and radiologic data of the dissemination of MS lesions in time and space. (Compston A, Coles A, October 2008, "Multiple sclerosis". *Lancet* 372 (9648): 1502-17; McDonald W I, Compston A, Edan G et al., July 2001, "Recommended diagnostic criteria for multiple sclerosis: guidelines from the International Panel on the diagnosis of multiple sclerosis". *Ann. Neurol.* 50 (1): 121-7; and Polman C H, Reingold S C, Edan G et al., December 2005, "Diagnostic criteria for multiple sclerosis: 2005 revisions to the "McDonald Criteria"". *Ann. Neurol.* 58 (6): 840-6).

The most commonly used diagnostic tools for MS are neuroimaging, analysis of cerebrospinal fluid and evoked potentials. In a positive diagnosis, magnetic resonance imaging (MRI) of the brain and spine shows areas of demyelination (lesions or plaques). Gadolinium administered, as a contrast agent, to a patient with MS typically localizes in these "hot spots" or lesions, and can be easily identified with the use of MRI. The MRI of the lesions is one of the most efficient methods of diagnosing MS. Measuring the development of new lesions is also a critical and efficient method of monitoring the progression of MS.

MS can be alternatively diagnosed with other known methods. For instance, it is known that an MS patient responds less actively to stimulation of the optic nerve (which may be examined using visual and sensory evoked potentials) and sensory nerves due to demyelination of these nerve pathways. (Gronseth G S, Ashman E J, May 2000, "Practice parameter: the usefulness of evoked potentials in identifying clinically silent lesions in patients with suspected multiple sclerosis (an evidence-based review): Report of the Quality Standards Subcommittee of the American Academy of Neurology". *Neurology* 54 (9): 1720-5). Chronic inflammation of the central nervous system can be demonstrated by an analysis of cerebrospinal fluid. The cerebrospinal fluid is tested for oligoclonal bands, which are present in 75-85% of people with MS. (McDonald W I, Compston A, Edan G, et al., July 2001; and Link H, Huang Y M, November 2006, "Oligoclonal bands in multiple sclerosis cerebrospinal fluid: an update on methodology and clinical usefulness". *J. Neuroimmunol.* 180 (1-2): 17-28).

The subject chosen for treatment according to an embodiment of the invention such as, for example, the identified MS patient, can be irradiated or illuminated with light from an appropriate light source. The term "light", as used herein, encompasses electromagnetic radiation at wavelengths visible to a human eye as well as that within an ultraviolet (UV) and near-infrared (near-IR) portions of the spectrum.

The term "light source" generally refers to single or multiple mechanisms or systems serving as a source of illumination inclusive of a light emitter and optical elements that may gate or shape the illumination. Thus, for example, a reflective surface such as a mirror redirecting at least a portion of light incident upon it, or a photorefractive element such as a lens, or a spectral filter operating either in transmission or reflection that is illuminated with the light from the light emitter is included within the meaning of a "light source". A light source may be used, e.g., for illumination of the MS patient.

The term "irradiance" is used to describe surface density of light incident on a reference surface in terms of radiant power per unit area or, alternatively, in terms of radiant energy per unit area. "Intensity" refers to spatial density of light expressed, for example, as radiant power per unit solid angle or as radiant energy per unit solid angle.

In one embodiment, a light source may include a light emitter generating light, whether at a predetermined wavelength or within at least one spectral band of interest, directly illuminating the patient with intensity and/or irradiance that generally depend on a mutual positioning of the light source and the patient. For example, and without loss of generality, a light emitter such as a fluorescent tube, or a mercury vapor light, or a light-emitting diode (LED), or an incandescent lamp may be used to emit UV light towards the patient.

In the present invention, a preferable light source is chosen to emit light within the UV-band (e.g., below approximately 400 nm) and, more particularly, within the UV-B band, defined as a spectral region between approximately 280 and 315 nm, or in a separate embodiment, within the UV-A band. In another embodiment of the present invention, the spectral region is between approximately 280 and 290 nm. In an alternative embodiment of the present invention, the spectral region is between 290 and 300 nm. In yet another embodiment of the present invention, the spectral region is between 300 and 315 nm. Various levels of patient-exposure to illumination are within the scope of this invention and, in a specific embodiment, the light source should be configured to assure patient irradiance of at least 2.5 kJ/m$^2$. In another embodiment of the invention, the light source also emits non-UV light.

According to embodiments of the invention, the light emitter may be supplemented with auxiliary optical component or a plurality of components that modifies spatial distribution of light emitted by the light emitter. For example, the light source may comprise a reflector intercepting at least a portion of emitted light and redirecting it towards the subject. Such a reflector may contain a generally curved reflective surface and, in particular, may incorporate a flat mirror or an optical diffractive element such as a diffractive grating. In a specific embodiment, a reflector may include a parabolic reflecting surface that at least partially collimates light emitted by the light emitter positioned at the focal point of the reflector and redirects this light towards the patient that is located at a specified distance from the light emitter.

In another embodiment, the light source may contain an optical system including at least one lens that is used to deliver substantially collimated light towards the patient. In such a light source, a light emitter such as a LED may be disposed at or near the focal point of the optical system. Alternatively, an optical system including at least one lens may be configured to shape the emitted light into a non-collimated beam that is further directed towards the subject, which is located at such a distance from the light emitter at to assure the exposure of the subject to the produced illumination at specified levels of irradiance and/or intensity.

In yet another embodiment, the light source may be configured so as to illuminate the subject substantially from all directions. In such an embodiment, the light source may comprise a reflector shaped generally as a three-dimensional elliptical chamber and substantially surrounding both the light emitter disposed at or near one focal point of the chamber and the subject located at another focus of the chamber. It is appreciated that, in this case, substantially all of the emitted light will be reflected by the internal walls of the chamber towards the subject.

In a related embodiment of the invention, the light source may include an emitter emitting light within a broad spectral range and at least one spectral filter intercepting the emitted light so as to filter out the light within a specific spectral band that is preferred for illumination of the subject. In one implementation where the subject should be illuminated with the UV-light, an optical filter transmitting the UV-light within the specified band (such as UV-B or UV-A) may be disposed across a collimated beam of light formed by the optical system of the light source and propagating towards the subject. A variety of known optical filters may be used for such purpose such as dichroic and multichroic filters, interference filters including thin-film filters, for example.

Illumination or irradiation of the subject with light from the light source of an embodiment of the invention may be generally carried out within a single time period, or repeatedly during several time-intervals, or even continuously, as required to achieve a particular level of light-exposure of the subject.

The overall length of irradiation or treatment is, preferably, defined by a degree of severity of MS exhibited by the patient. In one embodiment of the present invention, a patient may be exposed to light treatment until the most severe of his or her MS symptoms are abated or reduced. In another embodiment of the present invention, the patient may be exposed to light treatment on a daily basis for as long as relief from MS symptoms is desired.

In one embodiment of the present invention, subjects would be irradiated daily for at least 10 minutes, preferably 10-30 minutes, at a distance of at least 40 cm from the UV light source. Typically, treatment would be at least 7 days. One may wish to extend treatment either every day or every other day or every third day for the duration of the treatment. In another embodiment, patients may be irradiated with a lower dose of light but a longer, in some embodiments continuous, interval of light exposure. For example, one may wish to replace a house-hold light source with a light source capable of emitting a UV light dose suitable for the present invention.

One would monitor the patient's MS symptoms and detect a reduction or delay in these symptoms. Most preferably, the development of new lesions in the subject would be monitored on a regular (i.e., semi-annual) basis via MM as discussed above. Further symptoms that may be monitored include those selected from the group consisting of changes in sensation (hypoesthesia and paraesthesia), muscle weakness, muscle spasms, or difficulty in moving; difficulties with coordination and balance (ataxia); problems in speech (dysarthria) or swallowing (dysphagia), visual problems (nystagmus, optic neuritis, or diplopia), fatigue, acute or chronic pain, and bladder and bowel difficulties. Cognitive impairment of varying degrees and emotional symptoms of depression or unstable mood are also common. One common clinical measure of disability progression and symptom severity is the Expanded Disability Status Scale or EDSS.

"Reduction" in MS symptoms is defined to include any significant reduction (at least 30%) of MS symptoms. For instance, in one embodiment, after six months of daily treatment with the method of the present invention one would expect to see at least a 30% reduction in the amount of new lesions as compared to a MS patient without the treatment of the present invention.

"Delay" of MS symptoms is defined to include a significant delay (at least 30%) in the development of MS symptoms. For instance, in one embodiment, after six months of daily treatment with the method of the present invention one would expect to see at least 30% reduction in the symptoms associated with the lesions on the patients nervous system. With fewer lesions, one would expect less corresponding symptoms, including a delay in, for instance, the appearance of episodic acute periods of worsening (i.e. relapses, exacerbation, bouts, attacks, or flare ups). These episodic periods are also susceptible to reduction and delay and are within the scope of the present invention.

It is appreciated that implementation and/or operation of the embodiment of the invention, as discussed below—including but not limited to optional calibration and/or tuning of the employed light source, irradiation of the subject under test, detection of changes in clinical parameters, collection of data representing a process of irradiation and/or detected clinical parameters, and establishing an apparatus implemented in a computer system—is preferably enabled with the use of a processor controlled by instructions stored in a memory. The memory may be random access memory (RAM), read-only memory (ROM), flash memory or any other memory, or combination thereof, suitable for storing control software or other instructions and data. Various functions, operations, decisions, etc. of all or a portion of any embodiment of the invention may be implemented as computer program instructions, software, hardware, firmware or combinations thereof. Those skilled in the art should also readily appreciate that instructions or programs defining the elements of an embodiment of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Examples of Materials and Methodologies Used for Implementing Embodiments of the Invention Compounds.

$25(OH)D_3$ and $1,25(OH)_2D_3$ were synthesized by Sigma-Aldrich Fine Chemicals (Madison, Wis.). Compounds were dissolved in absolute ethanol, and the concentration was determined with an ultraviolet spectrophotometer using $\lambda_{max}$ of 264 nm and an extinction coefficient of 18,200 $M^{-1}$ $cm^{-1}$ for both compounds. Compounds were added to vegetable oil in the indicated concentrations and delivered in the purified diet as described below.

Animals and Diet.

Female C57BL/6 mice between 7-9 weeks of age were purchased from The Jackson Laboratory (Bar Harbor, Me.). All mice were housed at the University of Wisconsin-Madison Biotron animal facility under specific pathogen-free conditions and exposed to 12 h light-dark cycles. Prior to administration of experimental diets, mice were fed ad libitum standard rodent Labdiet® 5008 chow (Purina Mills International, Richmond, Ind.). In the indicated experiments, eight week old mice were switched to a purified diet containing all the essential nutrients for normal growth (Smith S M, Levy N S, & Hayes C E, 1987, Impaired immunity in vitamin A-deficient mice. *J Nutr* 117(5):857-865). $25(OH)D_3$ and $1,25(OH)_2D_3$ were added to the purified diet at doses ranging from 0-1000 μg per kilogram body weight per day. The diet was delivered in solidified agar form three times per week beginning 10 days prior to immunization and continued until the termination of the experiment. Animal protocols were approved by the University of Wisconsin-Madison Institutional Animal Care and Use Committee.

UV Irradiation.

During preparation, mice from the control and UV-treated groups were shaved with electric clippers one day before initiating UV-therapy. In one embodiment, UV-treated mice were irradiated with a bank of four unfiltered FS20T12 fluorescent sunlamps (Solarc Systems, Barrie, ON) emitting UVR within a broad band of 280-360 nm. Approximately 65% of the light-output was in the UVB-range (290-320 nm). The radiation output was measured, prior to each treatment, with the use of a UVX radiometer equipped with a 302 nm sensor (UVP, Upland, Calif.). Mice were individually irradiated in a 16-chamber plexiglass cage specifically designed to prevent mice from shielding each other from the UVR. Because of the possibility that the UVB-light output was unequal in the different chambers, mice were rotated through the different chambers on successive days. Mice were irradiated daily for either 13 minutes (2.5 kJ/m$^2$) or 26 minutes (5.0 kJ/m$^2$) at a distance of 40 cm from the UV-light source. In the UV-pretreatment study, mice were treated once daily with either 2.5 kJ/m$^2$ or 5.0 kJ/m$^2$ for a total of seven days. In the repeated irradiation UV study, mice were treated once daily with 2.5 kJ/m$^2$ for seven days, then either every other day or every third day with 2.5 kJ/m$^2$ UVB for the duration of the experiment.

Induction of EAE.

Myelin oligodendrocyte glycoprotein peptide (MOG$_{35-55}$) (MEVGWYRSPFSRVVHLYRNGK-SEQ ID NO:1) was synthesized at the University of Wisconsin-Madison Biotechnology Center and purified to ≥95% by reverse-phase HPLC. The MOG$_{35-55}$ peptide was resuspended in sterile PBS to a concentration of 4 mg/ml, then emulsified with an equivalent volume of complete Freund's adjuvant (CFA) supplemented with 5 mg/ml inactivated *Mycobacterium tuberculosis* H37Ra (DIFCO Laboratories, Detroit, Mich.). EAE was induced in 9-week old C57BL/6 mice by subcutaneous injection of 100 μl of MOG$_{35-55}$/CFA homogenate delivering 200 μg of MOG$_{35-55}$ peptide. On the day of immunization and 48 h later, mice were injected intraperitoneally with 200 ng of pertussis toxin (List Biological Laboratories, Campbell, Calif.) diluted in sterile PBS. Mice were scored daily for clinical signs of EAE using the following scale: 0, no clinical disease; 1, loss of tail tone; 2, unsteady gait; 3, hind limb paralysis; 4, forelimb paralysis; 5, death. Scoring was performed by the same individual throughout the experiment to ensure consistency. On selected days mice were independently scored by a different individual for comparison purposes, but the scores were not counted in the final analysis.

Analysis of Serum Calcium levels.

Blood samples were collected at the termination of the experiments and spun at 6000 rpm (2938 g) for 15 min, followed by a second spin at 14000 rpm (16883 g) for 1 min. Serum calcium levels were determined using the calcium L3K reagent (Genzyme Diagnostics, Charlottetown, PE Canada) and the ABX Pentra 400 clinical chemistry analyzer (Horiba-ABX Diagnostics, Irvine, Calif.).

Analysis of Serum $25(OH)D_3$ levels.

Blood samples were collected at selected time points throughout the experiment. Red blood cells were removed through two successive centrifugation steps as described above. Serum $25(OH)D_3$ levels were determined using a $^{125}$I-radioimmunological assay following the manufacturer's instructions (DiaSorin, Stillwater, Minn.). Samples above the range of the standard curve were diluted prior to analysis. Radioactivity was quantified using a Cobra 5002 gamma scintillation counter (PerkinElmer, Shelton, Conn.).

Data Analysis.

Individual subjects (mice) were scored daily for signs of EAE, and the mean clinical score was calculated for each group. Average onset and severity were calculated in affected mice displaying a clinical score of ≥1.0 for a minimum of two consecutive days. The onset value was calculated by averaging the first day when clinical signs appeared. The severity value was determined by averaging the maximum disease score reached during the entire experiment. The cumulative disease index (CDI) was calculated by summing the clinical scores for each group for all time points collected and dividing by the number of mice per group. Statistical analysis was performed using the two-tailed Fisher exact probability test for incidence rates, the Mann-Whitney non-parametric test for clinical scores, and the unpaired Student's t test for all other measurements. A value of P<0.05 was considered statistically significant.

EXAMPLES OF EXPERIMENTAL RESULTS a) UV pretreatment slightly increases 25(OH)D$_3$ levels, but does not suppress EAE.

Figure 1:
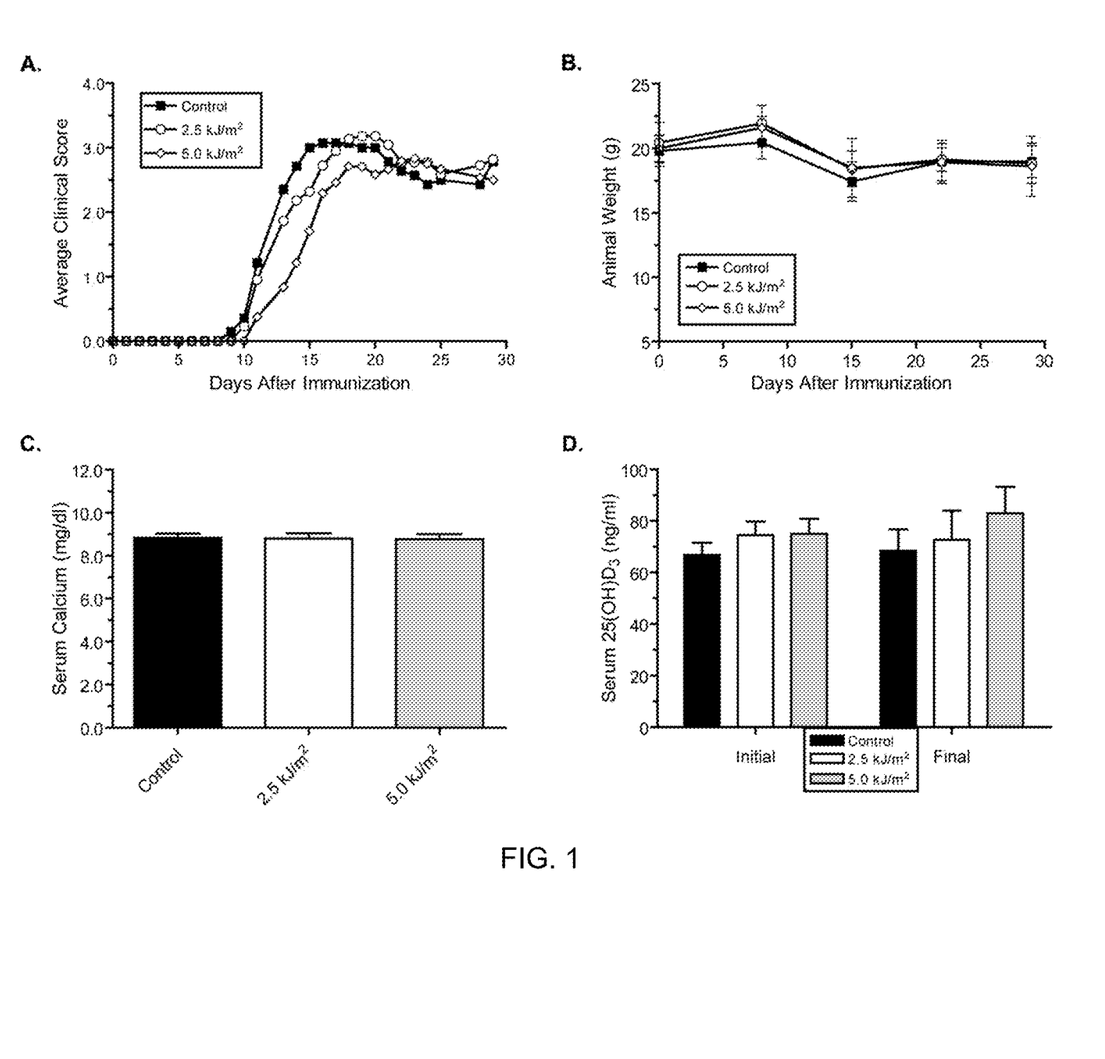
FIG. 1 shows that UVB pretreatment fails to suppress EAE and causes a slight increase in serum $25(OH)D_3$ levels. Mice were treated for 7 days prior to immunization with the indicated doses of UVB. (A) Average clinical EAE scores were determined daily for control and UVB treated mice (n=7-12). (B) Mice were weighed weekly (±SD) throughout the study to monitor disease-associated weight loss and toxicity. (C) Serum calcium levels (±SD) were determined at the end of the experiment using a clinical chemistry analyzer. (D) Serum $25(OH)D_3$ levels (±SD) were determined at the end of UV treatment and at the termination of the experiment.

Hauser et al. (1994) previously reported that the pretreatment with 2.5 kJ/m$^2$ of UVB light prevented induction of EAE in SJL mice. However, Hauser et al. did not determine the effects on vitamin D production and serum calcium levels. We attempted to confirm the Hauser findings in the myelin oligodendrocyte glycoprotein (MOG) model of EAE and to determine what effect UV treatment might have on vitamin D production and serum calcium levels. In one experiment, we irradiated subjects (female C57BL/6 mice) once daily for seven days with UVB-light with irradiance levels of 2.5 kJ/m$^2$ or 5.0 kJ/m$^2$. The subjects were immunized with MOG$_{35-55}$ following the last UV treatment and monitored daily for clinical signs of EAE. The light sources were appropriately positioned to assure that the mice receive the reported 2.5 kJ/m$^2$ used by Hauser et al. In contrast to Hauser et al., treatment with 2.5 kJ/m$^2$ of UVB-light had no significant effect on any of the clinical parameters that were tested (see Table 1 and FIG. 1A). Moreover, even the doubled UVB exposure (5.0 kJ/m$^2$) had no significant effect on clinical signs of EAE, although the onset appeared to be slightly delayed.

TABLE 1

UV pretreatment does not suppress clinical signs of EAE. Female C57BL/6 mice on a regular chow diet were treated once daily for seven days with either 2.5 kJ/m$^2$ or 5.0 kJ/m$^2$ UVB prior to immunization with MOG$_{35-55}$. The cumulative disease score (CDI) was calculated by summing all the clinical scores for the entire experiment and dividing by the number of mice for each group. The clinical data demonstrate the mean ± SD from one representative of 3 individual experiments.

| Treatment | Incidence | Day of Onset | Peak Severity | CDI |
|---|---|---|---|---|
| Control | 100% (7/7) | 11 ± 1 | 3.3 ± 0.4 | 43 ± 7 |
| 2.5 kJ/m$^2$ | 100% (11/11) | 12 ± 3 | 3.3 ± 0.5 | 42 ± 9 |
| 5.0 Kj/m$^2$ | 92% (11/12) | 14 ± 3 | 3.4 ± 0.6 | 36 ± 15 |

Vitamin D toxicity is known to cause weight loss and a dramatic rise in serum calcium levels. To assess the effect of UV treatment on these parameters, mice were weighed at selected time intervals throughout the study, and serum calcium levels were determined at the termination of the experiment. As shown in FIG. 1B, UVB-pretreatment did not significantly affect the weight of the mice. Furthermore, there were no detected difference in serum calcium levels at either the end of the UVB-pretreatment period (data not shown) or at the termination of the experiment (FIG. 1C). In addition, serum 25(OH)D$_3$ levels were determined both at the end of the UVB-pretreatment period and at the termination of the experiment. As shown in FIG. 1D, pretreatment with 2.5 kJ/m$^2$ and 5.0 kJ/m$^2$ UVB led to a slight increase, at the end of the UVB-pretreatment period, in serum 25(OH)D$_3$ levels (75 ng/ml) as compared to the control group (67 ng/ml). Corresponding levels of the 5.0 kJ/m$^2$ group remained elevated at the termination of the experiment. Thus, the conducted UVB-pretreatment did not cause vitamin D toxicity or hypercalcemia, and did not confer protection against the development or progression of EAE.

b) Repeated treatment with UV suppresses clinical signs of EAE.

Figure 2:
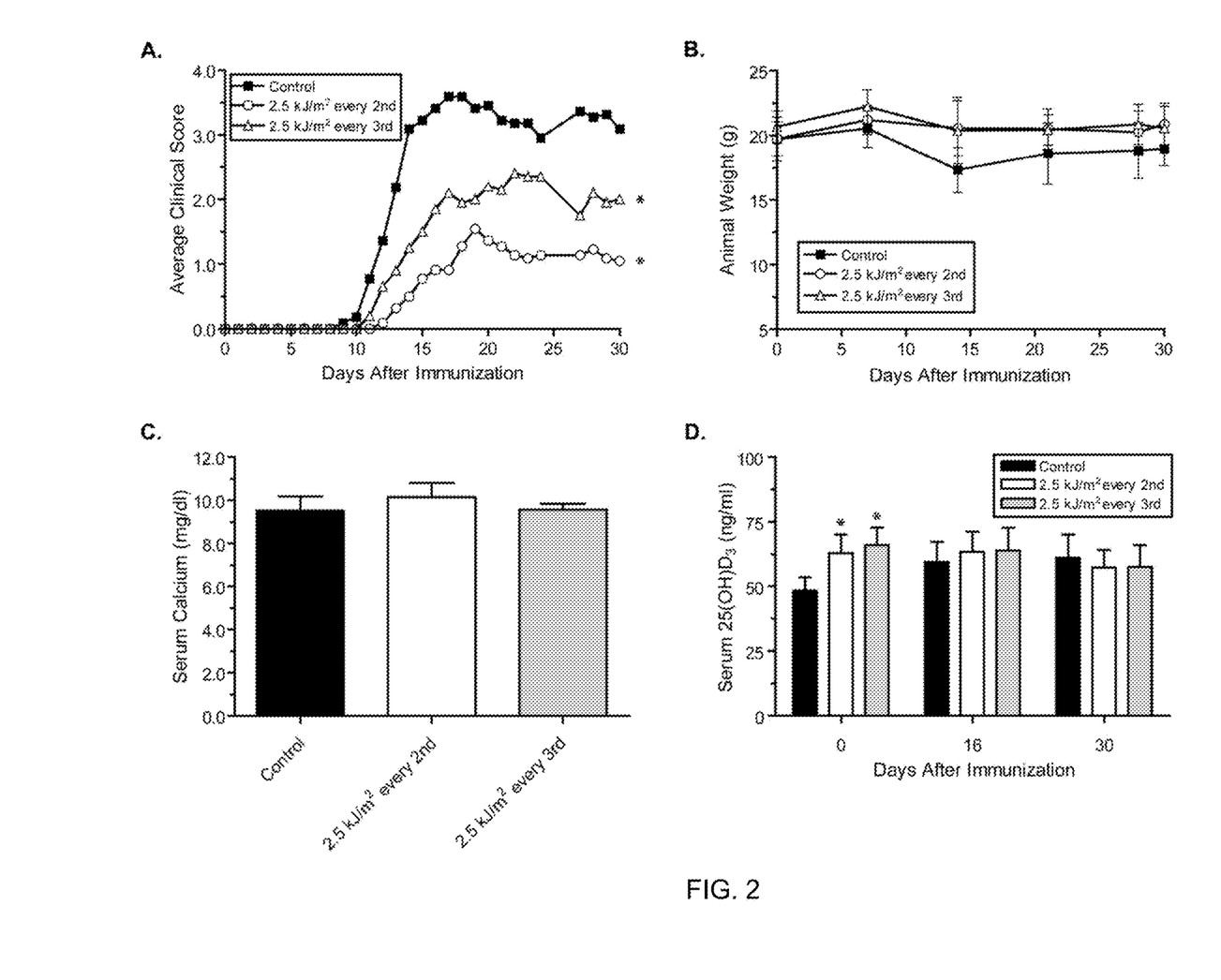
FIG. 2 illustrates that a repeated UVB treatment suppresses EAE and causes a transient increase in serum $25(OH)D_3$ levels. After immunization, mice were treated either every other or every third day with 2.5 kj/m2 UVB. (A) Average clinical EAE scores were determined daily for control and UVB treated mice (n=10-11). (B) Mice were weighed weekly (±SD) throughout the study to monitor disease-associated weight loss and toxicity. (C) Serum calcium levels (±SD) were determined at the end of the experiment using a clinical chemistry analyzer. (D) Serum $25(OH)D_3$ levels (±SD) were determined at selected time point throughout the experiment. *P<0.05 compared to control group.

Individuals living in equatorial regions are exposed to UVR on a daily basis for much of their lives. Although it is not possible to mimic the effects of a lifetime of UVR exposure in the lab, we reasoned that periodic (for example, daily) treatment with UVR throughout the experiment would provide a more realistic representation of UVR exposure in these regions. To determine the effect of daily UVR-treatment on EAE, mice were treated once daily with 2.5 kJ/m$^2$ UVB for seven days prior to immunization with MOG$_{35-55}$. Following the immunization, mice were additionally irradiated either every other day or every third day with 2.5 kJ/m$^2$ UVB-light for the duration of the experiment. As shown in Table 2, the incidence of EAE was not significantly decreased in either treatment group as a result of such irradiation. However, treatment with 2.5 kJ/m$^2$ every third day did cause a slight reduction in disease severity and a decrease in the cumulative disease index (CDI). A significant reduction in the average clinical EAE scores was also noted in this group (FIG. 2A). Increasing the frequency of UVB exposure to every other day enhanced the suppressive effect of the UVB treatment. Treatment with 2.5 kJ/m$^2$ UVB every other day significantly delayed the onset of the disease, reduced the peak severity, and decreased the CDI compared to the control group, as shown in Table 2. By "onset of the disease" we mean the presence of identifiable lesions in the patient's nervous system as identified via MRI. By "reducing peak severity" we mean reducing the number of new lesions. Increasing the frequency of UVB exposure also caused a further decrease in the average clinical EAE scores (FIG. 2A). Thus, irradiation with UVB-light was far more effective at suppressing EAE when treatment was delivered throughout the experiment, as opposed to the case when such irradiation was discontinued after the immunization of the subjects.

TABLE 2

Repeated UV-treatment inhibits EAE. Female C57BL/6 mice on a regular chow diet were treated once daily for seven days with 2.5 kJ/m$^2$ UVB prior to immunization with MOG$_{35-55}$. After immunization, mice were treated either every other or every third day with 2.5 kJ/m$^2$ UVB. The clinical data demonstrate the mean ± SD from one representative of 2 individual experiments.

| Treatment | Incidence | Day of Onset | Peak Severity | CDI |
|---|---|---|---|---|
| Control | 100% (11/11) | 12 ± 1 | 3.8 ± 0.7 | 54 ± 12 |
| 2.5 kJ/m$^2$ every 2$^{nd}$ day | 82% (9/11) | 17 ± 3* | 2.3 ± 0.9* | 17 ± 16* |
| 2.5 kJ/m$^2$ every 3$^{rd}$ day | 90% (9/10) | 14 ± 3 | 3.1 ± 0.9 | 32 ± 19* |

*P < 0.05 compared to the control group.

In addition to weight loss caused by vitamin D toxicity, mice can also lose weight due to muscle wasting and decreased food ingestion secondary to paralysis during the clinical course of EAE. The loss in weight correlated with severity of the disease in mice displaying more severe signs of disease. Mice treated every other day or every third day with 2.5 kJ/m$^2$ UVB did not lose as much weight as the control group (see FIG. 2B). Furthermore, the serum calcium levels in both UVB-treated groups were normal (FIG. 2C). Serum 25(OH)D$_3$ levels were significantly elevated on the day of immunization in both UVB-treated groups (FIG. 2D). However, 25(OH)D$_3$ levels did not remain elevated despite the continuation of UVB treatment. Thus, continuous UVB treatment caused significant suppression of clinical signs of EAE without elevating serum calcium levels and caused only a transient elevation of serum 25(OH)$D_3$ levels.

c) 25(OH)$D_3$ fails to prevent EAE at doses that cause severe hypercalcemia.

After establishing that continuous treatment with UVB suppresses EAE without dramatically increasing serum 25(OH)$D_3$ levels, we sought to determine if 25(OH)$D_3$ levels obtained upon UVB treatment were sufficient to suppress EAE without UVB treatment. Female C57Bl/6 mice were treated with either 10, 500, or 1000 µg/kg 25(OH)$D_3$ per day and compared to mice treated with vehicle or 2.5 µg/kg 1,25(OH)$_2D_3$ per day. Pilot studies indicated that treatment with 2.5 µg/kg of 1,25(OH)$_2D_3$ per day caused a dramatic suppression of clinical signs of EAE and was associated with severe hypercalcemia (data not shown). Consequently, this dose of 1,25(OH)$_2D_3$ served as a useful treatment group with which to compare the clinical and calcemic effects of 25(OH)$D_3$.

Figure 3:
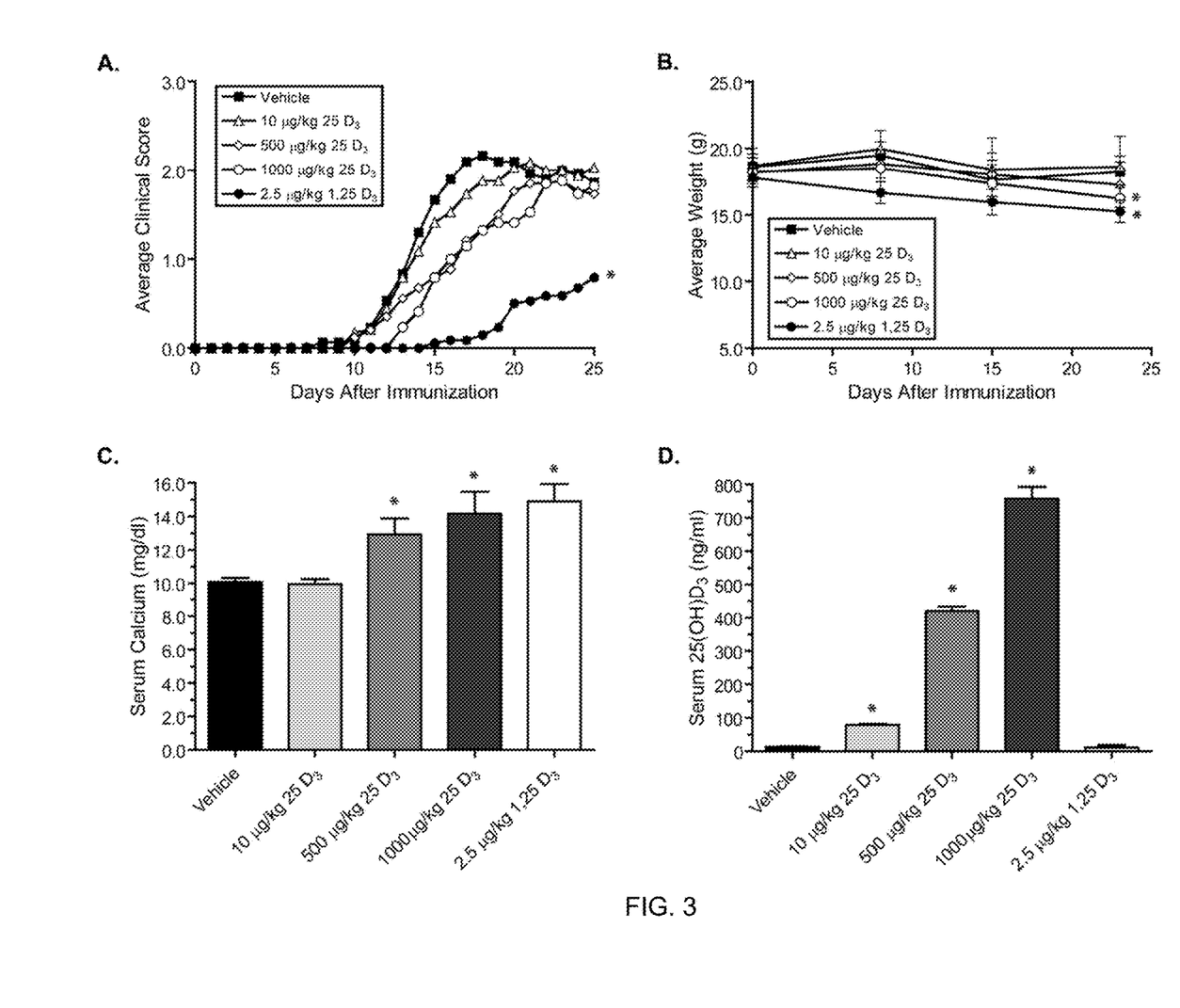
FIG. 3 shows that $25(OH)D_3$ only modestly suppresses EAE at doses that cause severe hypercalcemia. Beginning 10 days prior to immunization, mice were fed a purified 0.87% calcium diet delivering the indicated doses of either $25(OH)D_3$ or $1,25(OH)_2D_3$. Treatment continued for the duration of the experiment. (A) Average clinical EAE scores were determined daily for vehicle, $25(OH)D_3$, and $1,25(OH)_2D_3$-treated mice (n=15-17). (B) Mice were weighed weekly (±SD) throughout the study to monitor weight loss and toxicity. (C) Serum calcium levels (±SD) were determined at the end of the experiment using a clinical chemistry analyzer. (D) Serum $25(OH)D_3$ levels (±SD) were determined at the termination of the experiment. *P<0.05 compared to control group.

Treatment with 10 ug/kg of 25(OH)$D_3$ per day had no significant effect on the incidence, onset, severity, or progression of EAE (Table 3, FIG. 3A). Increasing the dose to 500 µg/kg per day caused a significant delay in the onset of disease and a slight suppression of clinical EAE scores. Further increasing the dose to 1000 µg/kg 25(OH)$D_3$ per day only slightly enhanced the suppressive effects seen in the 500 µg/kg 25(OH)$D_3$ treatment group causing a significant decrease in the CDI as well as a delay in the onset of clinical signs of disease compared to the vehicle group. Thus, even at a dose as high as 1000 µg/kg per day, 25(OH)$D_3$ caused only a modest suppression of EAE. In contrast, treatment with 2.5 µg/kg of 1,25(OH)$_2D_3$ led to a significant decrease in the disease incidence, delayed the onset, and dramatically decreased the CDI compared to the vehicle and 25(OH)$D_3$-treated groups.

Treatment with 1000 µg/kg of 25(OH)$D_3$ and 2.5 µg/kg of 1,25(OH)$_2D_3$ caused a significant decrease in the weight of the mice at the termination of the study (FIG. 3B). However, the drop in weight developed more slowly and was reduced in magnitude in the 1000 µg/kg 25(OH)$D_3$ group. Serum calcium levels were unchanged in mice treated with 10 µg/kg of 25(OH)$D_3$ (9.9 mg/dl) compared to the vehicle group (10.1 mg/dl) (FIG. 3C). In contrast, treatment with 500 µg/kg 25(OH)$D_3$ (12.9 mg/dl), 1000 µg/kg 25(OH)$D_3$ (14.2 mg/dl), and 2.5 µg/kg 1,25(OH)$_2D_3$ (14.9 mg/dl) all caused hypercalcemia. Although the elevation in serum calcium levels was similar in the 1000 µg/kg 25(OH)$D_3$ and 2.5 µg/kg 1,25(OH)$_2D_3$ treated groups, only 1,25(OH)$_2D_3$ prevented the induction of EAE (FIG. 3A). Thus, even at doses that dramatically elevated serum calcium levels and caused weight loss, 25(OH)$D_3$ provided only modest suppression of EAE. It is known that at high plasma levels of 25(OH)$D_3$, it acts as an analog of 1,25(OH)$_2D_3$ and increases serum calcium levels (Shepard R M & Deluca H F, 1980, Plasma concentrations of vitamin D3 and its metabolites in the rat as influenced by vitamin $D_3$ or 25-hydroxyvitamin D3 intakes. *Archives of Biochemistry and Biophysics* 202(1):43-53). Furthermore, this occurs in 1a-hydroxylase null mice (DeLuca, H. F., Prahl, J. and Plum, L. A., in preparation). Although 25(OH)$D_3$ acts as an analog elevating serum calcium levels, it may not express all of the functions of 1,25(OH)$_2D_3$ such as immunomodulation.

TABLE 3

25(OH)$D_3$ only modestly suppresses EAE. Female C57BL/6 mice were treated with either 25(OH)$D_3$ or 1,25(OH)$_2D_3$ in the indicated doses delivered in purified diet. All mice were immunized with MOG$_{35-55}$ 10 days after initiating therapy with the vitamin D metabolites. Mice were monitored daily for 25 days and assessed clinically for signs of EAE. The clinical data demonstrate the mean ± SD from one representative of 3 individual experiments.

| Treatment | Incidence | Day of Onset | Peak Severity | CDI |
|---|---|---|---|---|
| Vehicle | 87% (13/15) | 13 ± 2 | 2.7 ± 0.8 | 25 ± 10 |
| 10 µg/kg 25 $D_3$ | 88% (15/17) | 14 ± 3 | 2.9 ± 0.9 | 23 ± 16 |
| 500 µg/kg 25 $D_3$ | 82% (14/17) | 16 ± 4* | 2.7 ± 0.6 | 19 ± 12 |
| 1000 µg/kg 25 $D_3$ | 82% (14/17) | 16 ± 3* | 2.6 ± 0.6 | 17 ± 11* |
| 2.5 µg/kg 1,25 $D_3$ | 35% (6/17)† | 20 ± 3† | 2.3 ± 0.6 | 4 ± 7† |

*$P < 0.05$ compared to the vehicle group.
†$P < 0.05$ compared to all other groups.

Analysis of serum 25(OH)$D_3$ levels revealed that dietary administration of 25(OH)$D_3$ led to a dose-dependent increase of the 25(OH)$D_3$ metabolite in the serum of treated mice (FIG. 3D). Treatment with 10 µg/kg of 25(OH)$D_3$ resulted in serum 25(OH)$D_3$ levels similar to those seen upon continuous UVB treatment (FIGS. 2D and 3D). Notably, unlike with continuous UVB treatment, dietary administration of 10 µg/kg 25(OH)$D_3$ had no effect on EAE progression. This finding suggests that the serum 25(OH)$D_3$ levels obtained upon treatment with UVB are insufficient to suppress EAE and that UVB likely suppresses EAE independent of vitamin D production.

In contradistinction to Hauser et al., the seven-day pretreatment with 2.5 kJ/m² UVB did not suppress clinical signs of EAE. This discrepancy is potentially due to differences in mouse strains and antigens utilized in these studies or to differences in UV administration. Although UVB pretreatment failed to show an effect on EAE progression, continuous UVB treatment throughout the duration of the experiment caused, nevertheless, significant inhibition of EAE. This suggests that increasing the frequency of UVB exposure enhances its suppressive effects, and that the mechanisms underlying disease suppression may be transient and reversible.

Surprisingly, continuous UVB treatment only slightly elevated serum 25(OH)$D_3$ levels. Daily treatment with 2.5 kJ/m² UVB for seven days caused a modest increase of 16 ng/ml of 25(OH)$D_3$ in the serum. However, there was no difference in serum 25(OH)$D_3$ levels at later time points despite continued exposure to UVB. Further increases in 25(OH)$D_3$ levels may have been inhibited by mechanisms meant to prevent vitamin D toxicity. Clinical signs of EAE were observed to remain suppressed throughout the duration of the study, even when 25(OH)$D_3$ levels were no longer elevated compared to control mice. This suggests that sustained elevations of 25(OH)$D_3$ levels were not critical for the suppressive effects of UVB on EAE. This observation led us to explore the ability of 25(OH)$D_3$ delivered in the diet to suppress EAE independent of UVB exposure. Our results indicate that treatment with 10 µg/kg of 25(OH)$D_3$ had no effect on EAE despite causing an elevation in serum 25(OH)$D_3$ levels similar to that seen in the UVB-treated mice. Furthermore, treatment with up to 1000 µg/kg of 25(OH)$D_3$ caused only a modest suppression of EAE and was associated with severe hypercalcemia. In contrast, continuous treatment with 2.5 kJ/m² UVB led to greater disease suppression and had no effect on serum calcium levels. In humans, the normal range of serum 25(OH)$D_3$ levels is between 20-100 ng/ml (Holick M F (2009) Vitamin D status:

measurement, interpretation, and clinical application. *Ann Epidemiol* 19(2):73-78). Vitamin D toxicity occurs at serum 25(OH)$D_3$ levels above 200 ng/ml (Holick M F, 2009). The 25(OH)$D_3$ doses required to suppress EAE were well above this level. Thus, our data suggests that the 25(OH)$D_3$ levels obtained upon treatment with UVB are insufficient to suppress EAE, and that UVB is likely suppressing disease through mechanisms that are independent of vitamin D production.

The current model used to explain the relationship between increased UV exposure and decreased MS incidence is that UVR is critical for producing vitamin D which is then converted into 25(OH)$D_3$. Provided sufficient 25(OH)$D_3$ levels are present, 25(OH)$D_3$ can be converted to 1,25(OH)$_2D_3$ and perform immunoregulatory functions that suppress autoimmune mechanisms. Support for this hypothesis is derived from studies indicating that decreased exposure to UVR and decreased 25(OH)$D_3$ levels are associated with a higher risk for developing MS (Munger K L, Levin L I, Hollis B W, Howard N S, and Ascherio A, 2006, Serum 25-hydroxyvitamin D levels and risk of multiple sclerosis. *Jama* 296(23):2832-2838; and van der Mei I A, et al., 2007, Vitamin D levels in people with multiple sclerosis and community controls in Tasmania, Australia. *J Neurol* 254 (5):581-590). However, our results suggest that the levels of 25(OH)$D_3$ required to suppress EAE cannot feasibly be produced upon exposure to UVR.

UVR can suppress the immune system through a number of mechanisms independent of vitamin D, including inhibiting antigen presentation, altering inflammatory cytokine levels, and inducing suppressor T-cell populations (Norval M, McLoone P, Lesiak A, & Narbutt J, 2008, The effect of chronic ultraviolet radiation on the human immune system. *Photochem Photobiol* 84(1):19-28). Therefore, we suggest that UVR is likely playing a role in immunosuppression independent of vitamin D production. Potential caveats to this hypothesis include important differences between the immune systems of mice and humans (Mestas J and Hughes C C, 2004, Of mice and not men: differences between mouse and human immunology. *J Immunol* 172(5):2731-2738), as well as between MS and EAE (Steinman L and Zamvil S S, 2005, Virtues and pitfalls of EAE for the development of therapies for multiple sclerosis. *Trends Immunol* 26(11):565-571). Additionally, the electromagnetic radiation spectrum emitted by UV bulbs is not representative of sunlight and delivers a much higher proportion of UVB (Brown D B, et al., 2000, Common fluorescent sunlamps are an inappropriate substitute for sunlight. *Photochem Photobiol* 72(3):340-344). Despite these potential caveats, our data suggests that the putative benefits associated with exposure to UVR cannot be completely recapitulated by simple supplementation with vitamin D. In fact, the benefits of 25(OH)$D_3$ levels below the threshold that causes vitamin D toxicity and hypercalcemia would likely be negligible. Thus, at least some exposure to UVR may be necessary to prevent MS development. More work is required to determine the optimal levels of UVR exposure that provide the beneficial aspects of UVR while avoiding the detrimental effects associated with chronic UVR exposure.

Additional evidence linking vitamin D and MS is the observation that treatment with the active form of vitamin D, 1,25(OH)$_2D_3$, suppresses EAE (23, 24). However, the efficacy of 1,25(OH)$_2D_3$ treatment is closely linked with the hormone's ability to increase serum calcium levels; complete disease suppression only occurs using doses of 1,25 (OH)$_2D_3$ that cause severe hypercalcemia (26). Prolonged hypercalcemia can lead to the calcification of soft tissues such as kidney, heart, and liver, ultimately leading to organ failure. The hypercalcemic effects of 1,25(OH)$_2D_3$ have precluded its usage as a therapeutic agent in the treatment MS. A number of investigators have tried to overcome this limitation by developing less calcemic vitamin D analogs in hopes of reducing the calcemic effects while retaining the suppressive effects of the natural hormone (Lemire J M, Archer D C, and Reddy G S, 1994, 1,25-Dihydroxy-24-OXO-16ene-vitamin $D_3$, a renal metabolite of the vitamin D analog 1,25-dihydroxy-16ene-vitamin $D_3$, exerts immunosuppressive activity equal to its parent without causing hypercalcemia in vivo. *Endocrinology* 135(6):2818-2821, Mattner F, et al., 2000, Inhibition of Th1 development and treatment of chronic-relapsing experimental allergic encephalomyelitis by a non-hypercalcemic analogue of 1,25-dihydroxyvitamin D(3). *Eur J Immunol* 30(2):498-508; and van Etten E, et al., 2007, Novel insights in the immune function of the vitamin D system: synergism with interferon-beta. *J Steroid Biochem Mol Biol* 103(3-5):546-551). Despite modest success, no treatment involving 1,25 (OH)$_2D_3$ or vitamin D analogs has conclusively shown prevention of EAE without elevation of serum calcium levels. Moreover, results from our laboratory suggest that calcium may be playing an essential mechanistic role in 1,25(OH)$_2D_3$-mediated suppression of EAE (26, 28). These results diminish but do not eliminate the chance that an analog of 1,25(OH)$_2D_3$ can be found that may suppress MS. In contrast, continuous treatment with UVB suppresses EAE without altering serum calcium levels. Furthermore, there are no reported cases of hypercalcemia caused by excessive sunlight exposure (30). This suggests that disease suppression with UVR is independent of calcium, and that UVR is likely suppressing disease through different mechanisms than 1,25(OH)$_2D_3$.

Implementation of embodiments of the invention, as discussed above, suggest that continuous treatment with UVB suppresses clinical signs and symptoms of EAE. While UVB treatment causes a slight increase in serum 25(OH)$D_3$ levels, this elevation is insufficient to contribute to disease suppression. Furthermore, treatment with UVB did not elevate serum calcium levels, which appears to be a critical step in 1,25(OH)$_2D_3$-mediated suppression of EAE. Therefore, irradiation with UVB is likely to facilitate suppression of EAE independent of vitamin D production. While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

REFERENCES

1. Compston A & Coles A (2002) Multiple sclerosis. *Lancet* 359(9313):1221-1231.
2. Noseworthy J H, Lucchinetti C, Rodriguez M, & Weinshenker B G (2000) Multiple sclerosis. *N Engl J Med* 343(13):938-952.
3. Ebers G C (2008) Environmental factors and multiple sclerosis. *Lancet Neurol* 7(3):268-277.
4. Ebers G C & Sadovnick A D (1993) The geographic distribution of multiple sclerosis: a review. *Neuroepidemiology* 12(1):1-5.

5. Acheson E D, Bachrach C A, & Wright F M (1960) Some comments on the relationship of the distribution of multiple sclerosis to latitude, solar radiation, and other variables. *Acta Psychiatr Scand Suppl* 35(147):132-147.
6. Sutherland J M, Tyrer J H, & Eadie M J (1962) The prevalence of multiple sclerosis in Australia. *Brain* 85:149-164.
7. Freedman D M, Dosemeci M, & Alavanja M C (2000) Mortality from multiple sclerosis and exposure to residential and occupational solar radiation: a case-control study based on death certificates. *Occup Environ Med* 57(6):418-421.
8. Fisher M S & Kripke M L (1977) Systemic alteration induced in mice by ultraviolet light irradiation and its relationship to ultraviolet carcinogenesis. *Proc Natl Acad Sci USA* 74(4):1688-1692.
9. Kripke M L (1974) Antigenicity of murine skin tumors induced by ultraviolet light. *J Natl Cancer Inst* 53(5):1333-1336.
10. Leitenberger J, Jacobe H T, & Cruz P D, Jr. (2007) Photoimmunology—illuminating the immune system through photobiology. *Semin Immunopathol* 29(1):65-70.
11. McMichael A J & Hall A J (1997) Does immunosuppressive ultraviolet radiation explain the latitude gradient for multiple sclerosis? *Epidemiology* 8(6):642-645.
12. Tremlett H, et al. (2008) Monthly ambient sunlight, infections and relapse rates in multiple sclerosis. *Neuroepidemiology* 31(4):271-279.
13. Hauser S L, et al. (1984) Prevention of experimental allergic encephalomyelitis (EAE) in the SJL/J mouse by whole body ultraviolet irradiation. *J Immunol* 132(3):1276-1281.
14. Jones G, Strugnell S A, & DeLuca H F (1998) Current understanding of the molecular actions of vitamin D. *Physiological Reviews* 78(4):1193-1231.
15. Blunt J W, DeLuca H F, & Schnoes H K (1968) 25-hydroxycholecalciferol. A biologically active metabolite of vitamin D3. *Biochemistry* 7(10):3317-3322.
16. DeLuca H F (2004) Overview of general physiologic features and functions of vitamin D. *Am J Clin Nutr* 80(6 Suppl):1689S-1696S.
17. Holick M F, Schnoes H K, & DeLuca H F (1971) Identification of 1,25-dihydroxycholecalciferol, a form of vitamin D3 metabolically active in the intestine. *Proc Natl Acad Sci USA* 68(4):803-804.
18. Fraser D R & Kodicek E (1970) Unique biosynthesis by kidney of a biological active vitamin D metabolite. *Nature* 228(5273):764-766.
19. Hayes C E, Nashold F E, Spach K M, & Pedersen L B (2003) The immunological functions of the vitamin D endocrine system. *Cell Mol Biol (Noisy-le-grand)* 49(2):277-300.
20. Goldberg P (1974) Multiple Sclerosis: Vitamin D and calcium as environmental determinants of prevalence (a viewpoint). Part 1: Sunlight, dietary factors, and epidemiology. *International Journal of Environmental Studies* 6:19-27.
21. Lucas R M & Ponsonby A L (2006) Considering the potential benefits as well as adverse effects of sun exposure: can all the potential benefits be provided by oral vitamin D supplementation? *Prog Biophys Mol Biol* 92(1):140-149.
22. Munger K L, Levin L I, Hollis B W, Howard N S, & Ascherio A (2006) Serum 25-hydroxyvitamin D levels and risk of multiple sclerosis. *Jama* 296(23):2832-2838.
23. Lemire J M & Archer D C (1991) 1,25-dihydroxyvitamin D3 prevents the in vivo induction of murine experimental autoimmune encephalomyelitis. *J Clin Invest* 87(3):1103-1107.
24. Cantorna M T, Hayes C E, & DeLuca H F (1996) 1,25-Dihydroxyvitamin D3 reversibly blocks the progression of relapsing encephalomyelitis, a model of multiple sclerosis. *Proc Natl Acad Sci USA* 93(15):7861-7864.
25. Nashold F E, Hoag K A, Goverman J, & Hayes C E (2001) Rag-1-dependent cells are necessary for 1,25-dihydroxyvitamin D(3) prevention of experimental autoimmune encephalomyelitis. *J Neuroimmunol* 119(1):16-29.
26. Cantorna M T, Humpal-Winter J, & DeLuca H F (1999) Dietary calcium is a major factor in 1,25-dihydroxycholecalciferol suppression of experimental autoimmune encephalomyelitis in mice. *Journal of Nutrition* 129(11):1966-1971.
27. Holick M F, MacLaughlin J A, & Doppelt S H (1981) Regulation of cutaneous previtamin D3 photosynthesis in man: skin pigment is not an essential regulator. *Science* 211(4482):590-593.
28. Meehan T F, Vanhooke J, Prahl J, & Deluca H F (2005) Hypercalcemia produced by parathyroid hormone suppresses experimental autoimmune encephalomyelitis in female but not male mice. *Arch Biochem Biophys* 442(2):214-221.
29. Shepard R M & Deluca H F (1980) Plasma concentrations of vitamin D3 and its metabolites in the rat as influenced by vitamin D3 or 25-hydroxyvitamin D3 intakes. *Archives of Biochemistry and Biophysics* 202(1):43-53.
30. Holick M F (2009) Vitamin D status: measurement, interpretation, and clinical application. *Ann Epidemiol* 19(2):73-78.
31. van der Mei I A, et al. (2007) Vitamin D levels in people with multiple sclerosis and community controls in Tasmania, Australia. *J Neurol* 254(5):581-590.
32. Norval M, McLoone P, Lesiak A, & Narbutt J (2008) The effect of chronic ultraviolet radiation on the human immune system. *Photochem Photobiol* 84(1):19-28.
33. Mestas J & Hughes C C (2004) Of mice and not men: differences between mouse and human immunology. *J Immunol* 172(5):2731-2738.
34. Steinman L & Zamvil S S (2005) Virtues and pitfalls of EAE for the development of therapies for multiple sclerosis. *Trends Immunol* 26(11):565-571.
35. Brown D B, et al. (2000) Common fluorescent sunlamps are an inappropriate substitute for sunlight. *Photochem Photobiol* 72(3):340-344.
36. Lemire J M, Archer D C, & Reddy G S (1994) 1,25-Dihydroxy-24-OXO-16ene-vitamin D3, a renal metabolite of the vitamin D analog 1,25-dihydroxy-16ene-vitamin D3, exerts immunosuppressive activity equal to its parent without causing hypercalcemia in vivo. *Endocrinology* 135(6):2818-2821.
37. Mattner F, et al. (2000) Inhibition of Th1 development and treatment of chronic-relapsing experimental allergic encephalomyelitis by a non-hypercalcemic analogue of 1,25-dihydroxyvitamin D(3). *Eur J Immunol* 30(2):498-508.
38. van Etten E, et al. (2007) Novel insights in the immune function of the vitamin D system: synergism with interferon-beta. *J Steroid Biochem Mol Biol* 103(3-5):546-551.
39. Smith S M, Levy N S, & Hayes C E (1987) Impaired immunity in vitamin A-deficient mice. *J Nutr* 117(5):857-865.

40. www.wikipedia.com; Multiple Sclerosis
41. Compston A, Coles A (October 2008). "Multiple sclerosis". *Lancet* 372 (9648): 1502-17.
42. Trojano M, Paolicelli D (November 2001). "The differential diagnosis of multiple sclerosis: classification and clinical features of relapsing and progressive neurological syndromes". *Neurol. Sci.* 22 (Suppl 2): S98-102.
43. Poser C M, Brinar V V (June 2004). "Diagnostic criteria for multiple sclerosis: an historical review". *Clin Neurol Neurosurg* 106 (3): 147-58.
44. McDonald W I, Compston A, Edan G, et al. (July 2001). "Recommended diagnostic criteria for multiple sclerosis: guidelines from the International Panel on the diagnosis of multiple sclerosis". *Ann. Neurol.* 50 (1): 121-7.
45. Polman C H, Reingold S C, Edan G, et al. (December 2005). "Diagnostic criteria for multiple sclerosis: 2005 revisions to the "McDonald Criteria"". *Ann. Neurol.* 58 (6): 840-6.
46. Rashid W, Miller D H (February 2008). "Recent advances in neuroimaging of multiple sclerosis". *Semin Neurol* 28 (1): 46-55.
47. Link H, Huang Y M (November 2006). "Oligoclonal bands in multiple sclerosis cerebrospinal fluid: an update on methodology and clinical usefulness". *J. Neuroimmunol.* 180 (1-2): 17-28.
48. Gronseth G S, Ashman E J (May 2000). "Practice parameter: the usefulness of evoked potentials in identifying clinically silent lesions in patients with suspected multiple sclerosis (an evidence-based review): Report of the Quality Standards Subcommittee of the American Academy of Neurology". *Neurology* 54 (9): 1720-5.
49. Kurtzke J F (1983). "Rating neurologic impairment in multiple sclerosis: an expanded disability status scale (EDSS)". *Neurology* 33 (11): 1444-52.

We claim:

1. A method for suppressing clinical symptoms of multiple sclerosis (MS) in a subject in need thereof, the method consisting of:

(a) irradiating the subject with one or more doses of light from a light source; wherein the one or more doses of light comprise an energy density of at least 2.5 kJ/m$^2$ and is characterized by a wavelength of 280-360 nm; and wherein the one or more doses of light is effective to suppress multiple sclerosis symptoms, and (b) detecting a suppression of the clinical symptoms in the subject.

2. A method according to claim 1, wherein the suppression of the clinical symptoms includes at least one of a delay of onset of MS symptoms, a reduction of peak of severity of MS symptoms, and a decrease of the cumulative disease index (CDI).

3. A method according to claim 1, wherein the suppression of the clinical symptoms includes delay or reduction in the appearance of plaques or lesions.

4. A method according to claim 1, wherein the one or more doses of light is administered for at least 10 minutes every 24 hours for at least seven days.

5. A method according to claim 4, wherein the every 24 hour administration continues for 6 months.

6. The method of claim 1, wherein at least 65% of the light in the one or more doses of light is of wavelength 290-320 nm.

7. A method according to claim 1, wherein the one or more doses of light is administered for at least 10 minutes every other day for at least 7 days.

8. A method according to claim 7, wherein the every other day administration continues for 6 months.

9. A method according to claim 1, wherein one or more doses of light is administered for at least 10 minutes every third day for at least 7 days.

10. A method according to claim 9, wherein the every third day administration continues for 6 months.

* * * * *

UNITED STATES PATENT AND TRADEMARK OFFICE
CERTIFICATE OF CORRECTION

PATENT NO. : 11,260,241 B2
APPLICATION NO. : 16/131544
DATED : March 1, 2022
INVENTOR(S) : Hector F. Deluca et al.

It is certified that error appears in the above-identified patent and that said Letters Patent is hereby corrected as shown below:

In the Specification

Column 10, Line 21, "via MM as" should be --via MRI as--.

Signed and Sealed this
Seventh Day of June, 2022

Katherine Kelly Vidal
*Director of the United States Patent and Trademark Office*